United States Patent
Landfors et al.

(10) Patent No.: US 12,343,219 B2
(45) Date of Patent: Jul. 1, 2025

(54) ENVIRONMENT CAPTURE MANAGEMENT TECHNIQUES

(71) Applicant: GYRUS ACMI, INC., Westborough, MA (US)

(72) Inventors: Kurt B. Landfors, Acton, MA (US); Thomas Michael Thornton, Harvard, MA (US); Geophrey J. McComis, Leominster, MA (US)

(73) Assignee: GYRUS ACMI, INC., Westborough, MA (US)

( * ) Notice: Subject to any disclaimer, the term of this patent is extended or adjusted under 35 U.S.C. 154(b) by 542 days.

(21) Appl. No.: 17/585,176

(22) Filed: Jan. 26, 2022

(65) Prior Publication Data

US 2022/0233272 A1 Jul. 28, 2022

Related U.S. Application Data (60) Provisional application No. 63/142,734, filed on Jan. 28, 2021.

(51) Int. Cl.
*A61B 90/00* (2016.01)
*H04N 5/77* (2006.01)
*H04N 7/18* (2006.01)

(52) U.S. Cl.
CPC ............ *A61B 90/37* (2016.02); *A61B 90/361* (2016.02); *H04N 5/77* (2013.01); *H04N 7/181* (2013.01); *A61B 2560/0493* (2013.01)

(58) Field of Classification Search
CPC .................. A61B 90/37; A61B 90/361; A61B 2560/0493; G06V 20/49; G16H 20/40; G16H 30/20; G16H 40/20; G16H 40/67; G11B 27/031; H04N 5/77; H04N 7/181
See application file for complete search history.

(56) References Cited

U.S. PATENT DOCUMENTS

| | | | |
|---|---|---|---|
| 10,506,281 B1 * | 12/2019 | Mortensen | G06V 40/10 |
| 10,872,231 B2 * | 12/2020 | Vaidya | G08B 13/19695 |
| 2008/0144906 A1 * | 6/2008 | Allred | A61B 6/4441 |
| | | | 382/131 |

(Continued)

FOREIGN PATENT DOCUMENTS

WO  WO-2022164887 A1  8/2022

OTHER PUBLICATIONS

"International Application Serial No. PCT US2022 013877, International Search Report mailed Apr. 20, 2022", 4 pgs.

(Continued)

*Primary Examiner* — Sath V Perungavoor
*Assistant Examiner* — Paramita Ghosh
(74) *Attorney, Agent, or Firm* — Schwegman Lundberg & Woessner, P.A.

(57) ABSTRACT

A system can perform image capture during a medical procedure. The system can record video from one or more video sources. The system can store the recorded video in a cached memory as stored video. The system can receive a triggering event, such as receiving a signal, operation of an actuator, or issuance of a voice command. In response to the triggering event, the system can capture a video segment from the stored video. Because the video segment is captured from stored video, the video segment can optionally include video and/or frames that occurred before the triggering event is received.

21 Claims, 6 Drawing Sheets

(56) References Cited

U.S. PATENT DOCUMENTS

| | | | | |
|---|---|---|---|---|
| 2015/0199892 A1* | 7/2015 | Johnson | ................. | G08B 31/00 |
| | | | | 348/77 |
| 2015/0364158 A1* | 12/2015 | Gupte | ..................... | H04N 5/77 |
| | | | | 386/223 |
| 2016/0225408 A1* | 8/2016 | Khan | ..................... | G11B 27/34 |
| 2018/0322949 A1* | 11/2018 | Mohr | ..................... | G16H 40/63 |
| 2019/0287376 A1* | 9/2019 | Netscher | ................ | G08B 25/08 |
| 2021/0055537 A1* | 2/2021 | Komp | ................. | A61B 1/0005 |
| 2022/0222940 A1* | 7/2022 | Rawat | ................... | G06V 20/40 |

OTHER PUBLICATIONS

"International Application Serial No. PCT US2022 013877, Written Opinion mailed Apr. 20, 2022", 6 pgs.
"International Application Serial No. PCT/US2022/013877, International Preliminary Report on Patentability mailed Aug. 10, 2023", 8 pgs.

* cited by examiner

ENVIRONMENT CAPTURE MANAGEMENT TECHNIQUES

CROSS-REFERENCE TO RELATED APPLICATION

This patent application claims the benefit of U.S. Provisional Patent Application No. 63/142,734, filed Jan. 28, 2021, entitled "ENVIRONMENT CAPTURE MANAGEMENT TECHNIQUES", which is incorporated by reference herein in its entirety.

TECHNICAL FIELD

The present disclosure relates to archiving information and, more particularly, to techniques for capturing image and other information from a medical/clinical environment for later use.

BACKGROUND

An operating room can be a very dynamic environment. In addition to the activity of the primary operating doctor(s), other physicians and support personnel can be executing and completing countless other tasks as well as monitoring a variety of conditions to ensure the procedure progresses as planned or to be sure any unexpected conditions are addressed with the appropriate priority.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Medical professionals such as physicians, surgeons, or the like, can increasingly rely on the use of audio-visual (AV) recordings and images during and after medical procedures. For example, in some operating environments, audio and visual systems can allow remote specialists to assist on-site personnel during a procedure, as well as for review by the medical professionals after the procedure has ended. In some operating environments, the surgical site of a patient can be projected onto a large screen to assist the primary operating doctor in the procedure and to assist supporting physicians and personnel to understand the current state of the procedure. This can be especially true of procedures that include a medical scope such as an endoscope, laparoscope, ureteroscope, etc. that can include small optical sensors capable of capturing images at surgical sites relatively deep within a patient. An integrated operating room system can provide one or more of the above capabilities.

Disclosed herein are systems and techniques to enhance conventional integrated operating room systems by allowing one or more operating personnel such as a physician to capture and record certain instances of a procedure for review or training purposes. In addition, since certain interesting moments can be fleeting, the example system can buffer information and allow the user to set up parameters to capture the environment a certain time period before a physician triggers the system to perform a capture activity. In some examples, the parameters can also be programmed to allow gaps in capturing information.

In an example, a system for image capture during a medical procedure can comprise at least one processor and memory coupled to the at least one processor that, when executed by the at least one processor, cause the at least one processor to execute operations. The operations can comprise recording video or capturing still images from one or more video sources (e.g., one or more cameras), storing the recorded video in a cached memory as stored video, receiving a triggering event, and in response to the triggering event, capturing a video segment from the stored video. The operations can further comprise, prior to receiving the triggering event, buffering one or more segments of the stored video, and storing a modified video that includes the captured video segment prepended with the one or more buffered video segments. The modified video can be stored separately from the recorded video stored in the cache memory.

In an example, the operations can further comprise continuously recording a cached video stream from the one or more video sources and prepending one or more video frames of the cached video stream having a time code occurring prior to the triggering event. In an example, the operations can further comprise storing a video capture window of time (e.g., a five second window of time, or any suitable, desirable, or the like, window of time), and the video capture window of time can include at least a portion of the one or more buffered segments.

In an example, the operations can further comprise capturing a plurality of frames of the stored video, the plurality of frames extending over a time window that includes the triggering event and storing one or more still images from the plurality of frames of the stored video. The capturing of the plurality of frames can include selecting the time window/window of time based on one or more parameters such as values controlling the number of active content streams from which images are to be captured, desired temporal distribution of captured images, temporal spacing between captured frames of video, number of captured frames before and after a current frame at time of a valid capture and record request, desired spatial characteristics of captured frames, or combinations thereof.

Spatial characteristics can govern how the video from the one or more video sources is processed. The one or more spatial characteristics can include at least one of: interlacing, native image resolution, scaled image resolution, filtering, natural image color, image color correction, image dimension, or the like.

In an example, the operations can comprise, receiving one or more predetermined parameters and, prior to receiving the triggering event, buffering one or more segments of the stored video based on the one or more predetermined parameters. The operations can then include storing a modified video that includes the captured video segment prepended with the one or more buffered video segments based on the one or more predetermined parameters. The operations can also include capturing a plurality of frames of the stored video based on the one or more predetermined parameters, the plurality of frames extending over a time window/window of time that includes the triggering event and storing one or more still images from the plurality of frames.

Figure 1:
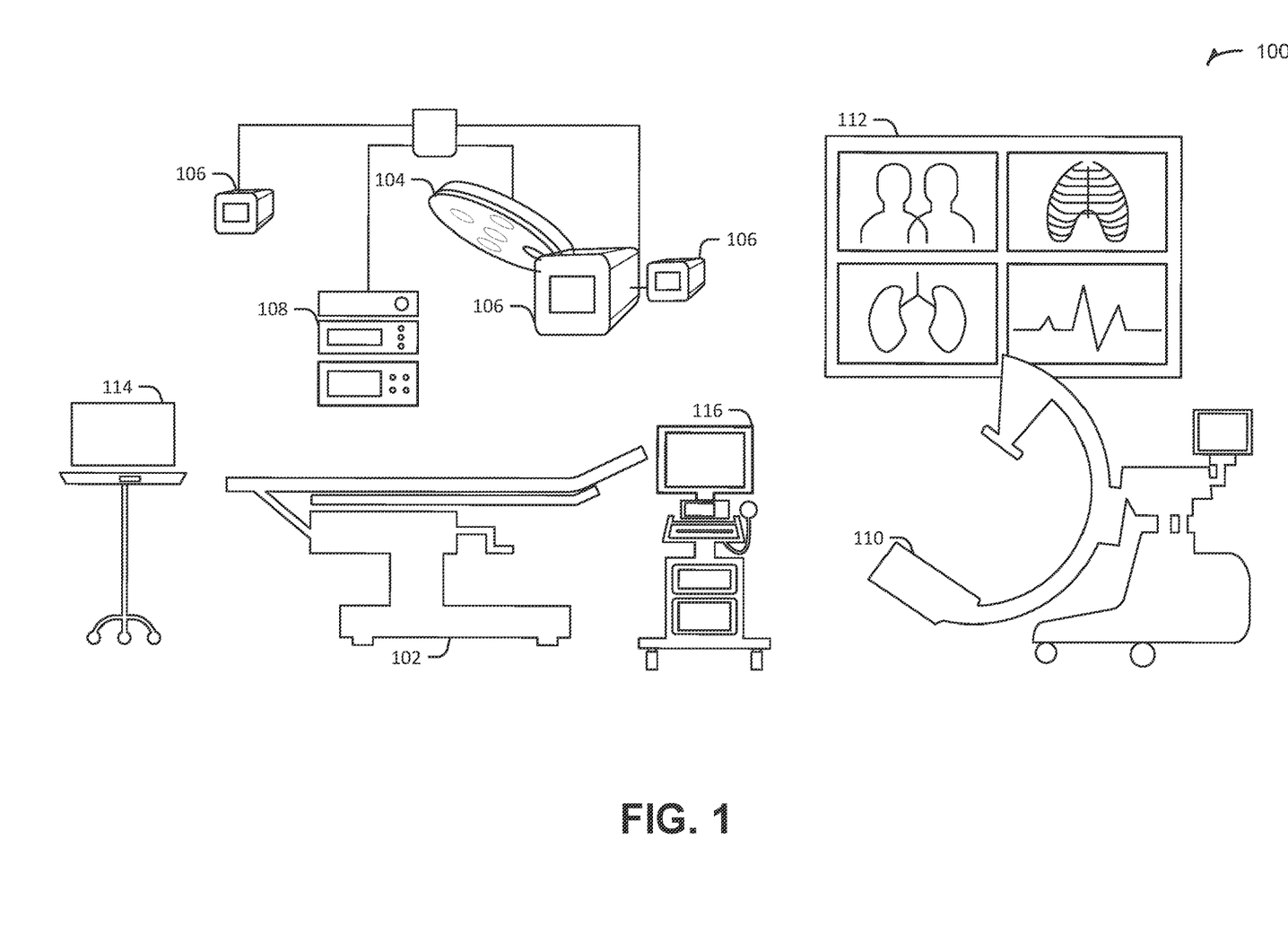
FIG. 1 illustrates generally an example of an integrated operating room.

FIG. 1 illustrates generally an example of an integrated operating room 100. The integrated operating room 100 can include an operating bed 102, one or more procedure tools (e.g., one or more scopes, such as an endoscope, laparoscope, or the like), one or more reference tools, one or more monitoring devices 108 (e.g., a heart rate monitor, a blood pressure monitor, and oxygen level monitor, or the like), one or more diagnostic devices/tools 110 (e.g., a portable x-ray machine, an ultrasound, or the like), one or more lights 104, one or more video sources such as cameras 106, one or more microphones, one or more speakers, and/or one or more displays 112 and 114.

In certain examples, some of the video sources in the integrated operating room 100, such as cameras 106, may be fixed in location with respect to the room (e.g., above the operating bed 102). Other video sources can be attached to various procedure tools, such as attached to an endoscope. During an operation, the displays 112, 114 can show views of one or more video sources, such as cameras 106, information from the monitoring devices 108, information from the one or more diagnostic devices 110, and/or images of other personnel remotely observing, or advising on, the procedure. The speakers can convey information from the remote participants, the local participants, or to provide entertainment audio. The microphones can communicate to the remote participants, to provide voice-control commands to the monitoring devices 108, the one or more lights 104, to a system controller 116, or to report events of the procedure. The system controller 116 can be located in the integrated operating room 100 (e.g., as a computer located in the room), in a server room in the same building as the integrated operating room 100, or offsite.

On or more actuators/actuation members can control any of the video sources in the integrated operating room 100, such as cameras 106 or cameras attached to the one or more procedure tool, such as an endoscope. The actuator can include a button located on the operating bed 102 or on the one or more procedure tools, the one or more monitoring devices 108, the one or more diagnostic tools 110, a foot pedal located next to the operating bed 102, or the like. A physician/surgeon can activate or operate the actuator to capture an image, video segment, or the like, from one or more of the cameras 106.

Figure 2:
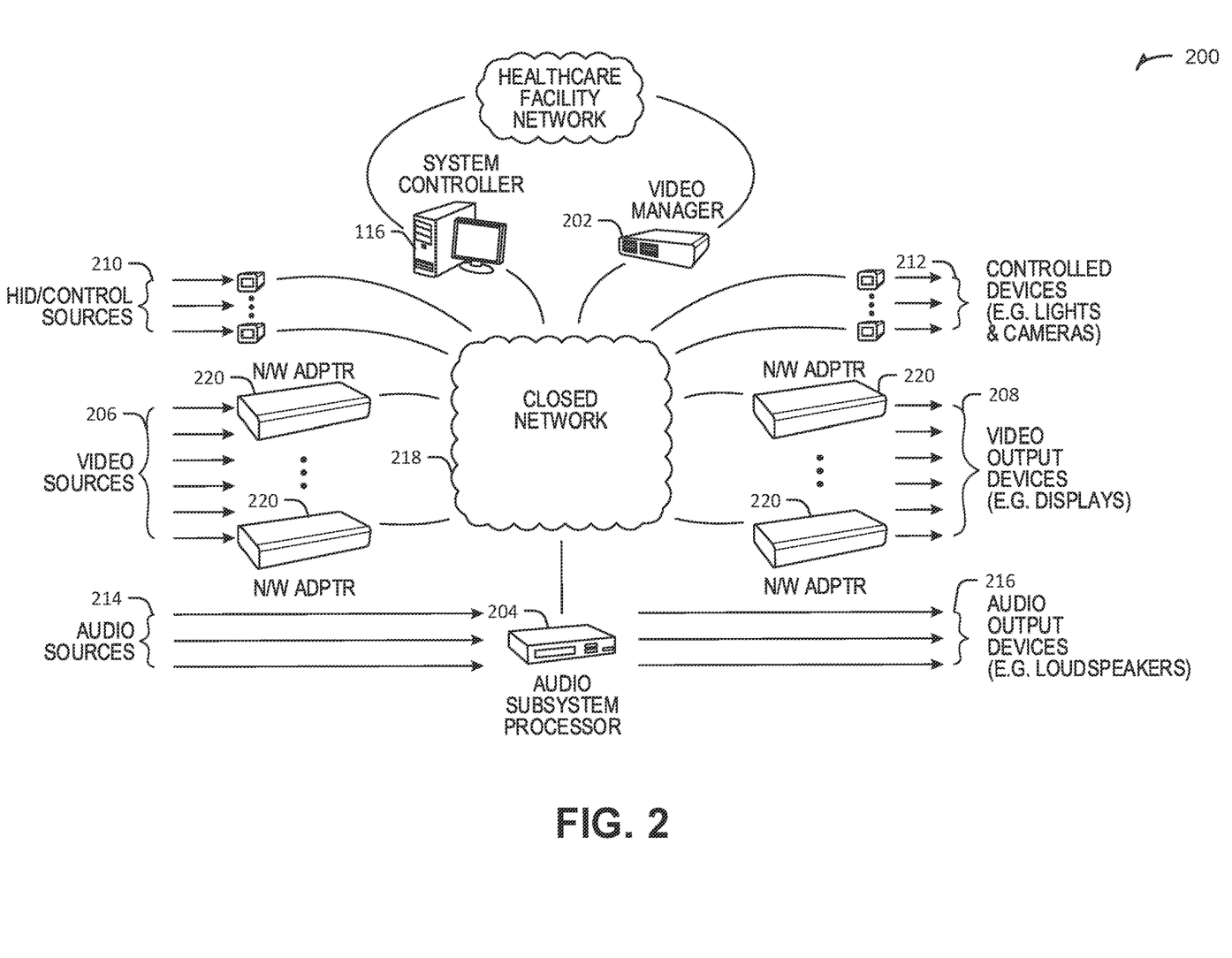
FIG. 2 illustrates generally a schematic of an example of an integrated system for the example integrated operating room of FIG. 1.

FIG. 2 illustrates generally a schematic of an example of an integrated system 200 (e.g., an integration system, audio-visual (AV) system, integrated audio-visual system (IAV), or a similar system) for the integrated operating room 100 of FIG. 1. The integrated system 200 can include a system controller 116, a video manager 202, an audio system processor 204, one or more video input adapters 206, one or more video output devices 208, one or more discrete input interfaces 210, and one or more controlled devices 212. The discrete input interfaces 210 can receive input information from human interface controls, such as pushbuttons, foot pedals, actuators, dials, the one or more monitoring devices 108, and/or the one or more diagnostic devices 110. Discrete output interfaces can provide control signals to the controlled devices 212 (e.g., one or more lights 104, the one or more video sources such as cameras 106, and the one or more monitoring devices 108, the one or more diagnostic devices 110, or the like).

The one or more video input adapters 206 can receive video signals form the various video sources, such as cameras 106, or cameras attached to the one or more procedure tools. The one or more video output devices 208 (e.g., monitors or other displays) can provide signals for displaying image or textual information on the one or more displays 112, 114. The video manager 202 can control the flow of video information received from the one or more video input adapters 206 and provided to the one or more video output devices 208. The audio system processor 204 can receive audio from multiple sources 214 and can route audio signals to multiple audio output devices 216 (e.g., speakers located in the integrated operating room 100 or located remote to or outside of the integrated operating room 100).

In certain examples, one or more of the system controller 116, video manager 202 or audio system processor 204 can capture and record a state of the system. For example, during a procedure, one or more of the personnel can instruct the system to capture and record an event of interest. In some examples, a user can program the system to buffer one or more aspects of the system at all times. For example, in some systems, one or more of the video feeds from the video sources, such as cameras 106 or cameras attached to a scope or any other procedure device can be buffered. As an interesting visual event occurs, the primary doctor/surgeon can request that video be captured and recorded. The system can buffer a video stream to capture video of an event and further capture video that occurred before the event. In particular, the buffering can allow the system to capture video that occurred before a practitioner issued a capture/record command. The buffering can allow the user to capture unexpected, interesting events even if those events are fleeting or over before the command to capture and record can be given.

The devices of the integrated system 200 can be connected or communicatively coupled, to each other such as through a network, such as closed network 218. The devices can be connected to the closed network 218 through one or more network adaptors 220. The closed network 218 may be a wireless local area network (WLAN), that allows only authorized devices such as the system controller 116, the video manager 202, the audio system processor 204, the one or more video input adapters 206, the one or more video output devices 208, or the one or more controlled devices 212 the ability to access and communicate over the closed network 218.

In some examples, a user can program the system with preferences or selections that govern how the system will respond to certain capture and record requests. These selections/preferences can be programmed and/or saved in a profile specific to one or more of: a particular surgeon/doctor/physician performing or assisting a medical procedure, specific to the type of medical procedure being performed, specific to the room the medical procedure is being performed in, or specific to the facility (e.g., the hospital or clinic) the medical procedure is being performed in. In a case in which a particular physician has profile information saved, and there are also preferences/selections saved for the facility or room, the system may combine, aggregate, or the like, the profile preferences/selections so that the system can capture, and/or record segments based on all the active preferences/selections.

One possible parameter that can be programmed is a buffer value. The buffer value can control how much buffered information (e.g., buffered video frames) occurring before receiving a request to capture and record (a capture request), a triggering event, or the like, is retrieved or added to the captured video. The buffered information can result in one or more buffered segments. These buffered segments can be fixed length or a length that is user modifiable. The length of the buffered segments can also depend on a recognized event of a medical procedure.

Another parameter, an event window/time window/window of time can set the amount of information to capture for each request. For example, for capturing and recording video, a user can program the system to capture and record X frames of buffered video and Y total frames event window in response to a capture and record request. As such, X frames of video before the request and quantity (Y−X) frames of video after the request can be recorded for a capture and record request.

Similarly, the system can continuously record a cached video stream from one or more of the video sources. The user can program the system to capture and record X frames of buffered video before a triggering event, T, and prepend one or more video frames of the cached video stream with the frames of buffered video. Likewise, the user can program the system to capture and record Y frames of buffered video that occur after the triggering event T and append one or more frames of the cached video streams with this buffered video. This can allow a user to capture a number of frames over a time window that includes frames having a time code that occurred before the capture request/triggering event, and frames having a time code that occurred after the triggering event.

In some examples, the system can allow a user to program a skip value. In terms of video information, the skip value can allow for one or more frames to be skipped for recording. The value can be helpful in saving recorded space for events that can take an extended period of time. As a numerical example, a user can program the system with an event window of 20 frames and a skip value of 3 frames. In response to a capture and record request, the system can capture and record a first frame, skip three frames, capture and record the fifth frame, skip three frames, capture and record the ninth frame, skip three frames, and so on until 20 frames are recorded. The system can record 20 frames that spans 77 frames of video (e.g., 20 captured frames+(19×3) skipped frames).

In some examples, the system can save captured frames as a video recording, such as a video clip or a video segment. In some examples, the system can save captured frames as still images from a video stream. For example, the system can capture frames over a time window, skip any desired frames, and store one or more still images from the frames of stored video.

In some examples, a user can trigger capturing the video segments. For example, the user can operate an actuator, such as by pressing a button, depressing a foot pedal, switching a switch, and others. By operating the actuator, the user can capture a portion of video or still imaged that reside in a cached or stored video feed. As another example, the user can issue a voice command to capture the video or images. As a specific example, the user can command the system to capture the last ten seconds of video. As another example, the user can command the system to start video capture. As another example, the user can command the system to stop video capture.

In some examples, a camera lingering/holding/pausing on a location for a specified duration can trigger capturing the video. For example, during an endoscopic procedure, the physician may pause while advancing the scope through a portion of a patient's anatomy to observe a particular piece of tissue, observe a mass, perform an ablation, or others. The system can automatically determine that the scope is no longer advancing/moving and trigger the video capture at the time the physician stopped moving the scope, and then end the video capture when the scope starts advancing again.

In some examples, the triggering event can be a specific point, time, event, or aspect occurring during a particular medical procedure. In such an example the system may be programmed to capture video during a medical procedure such as kidney stone ablation, orthoscopic knee surgery, or any other medical procedure. An artificial intelligence/trained machine learning algorithm can determine when a particular event occurs during the procedure (e.g., the ablation of a kidney stone, ablation of tissue, or ablation of a nerve) and trigger the video capture, and stop capturing the video when the event is determined to be concluded, finished, or the like.

Figure 3:
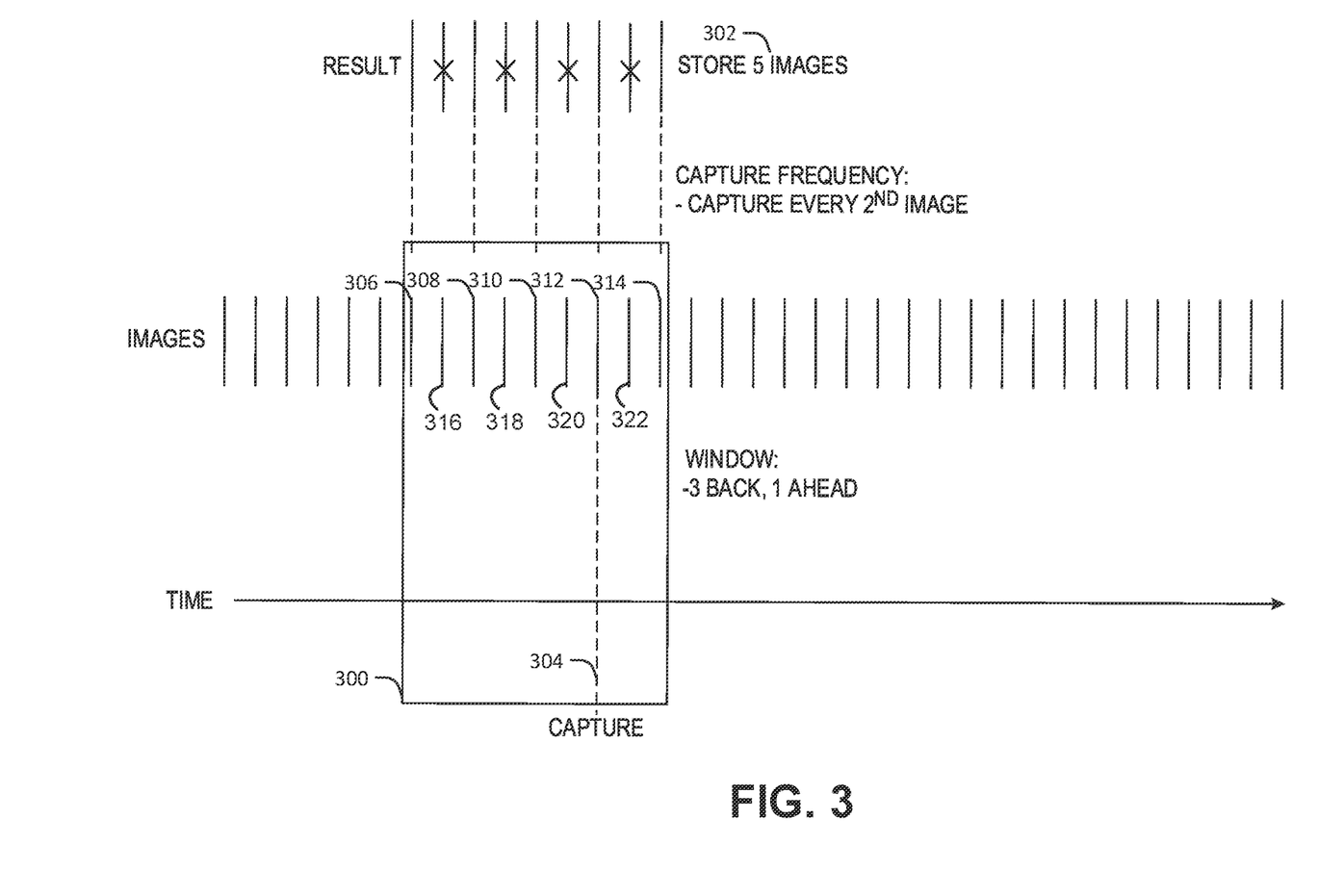
FIG. 3 illustrates graphically a capture and record method of an example system.

FIG. 3 illustrates graphically another capture and record method of an example system. The system can include parameters for responding to a capture and record request. For example, the system of FIG. 3 can have an event window 300 of five images 302, a buffered value of three images, and a skip value of one image. Upon receiving a capture request 304, the system can capture and record three buffered frames and two subsequent frames. The five recorded frames can be separated from each subsequent recorded frame or each prior recorded frame by one frame. Thus, frame one 306 can be recorded, frame two 316 skipped, frame three 308 recorded, frame four 318 skipped, frame five 310 recorded, frame six 320 skipped, frame seven 312 recorded, frame eight 322 skipped, and frame nine 314 recorded. As a result, the five recorded frames are frame one 306, frame three 308, frame five 310, frame seven 312, and frame nine 314, with frame seven 312 being the frame at which the capture request 304 was received by the system. It is understood that the values of the parameters above are for example purposes and that different implementation or name of the above parameters is possible without departing from the present subject matter.

As discussed above, in certain examples, the system can include programmable parameters that govern how the system will respond to capture requests. The programmable parameters can also govern performance characteristics of a clinical image capture system (e.g., governing the time window/window of time/number of frames of video captured by a capture request or triggering event). In certain examples, the parameters can include values controlling the number of active content streams from which images are to be captured, desired temporal distribution of captured images, temporal spacing between captured frames of video, number of captured frames before and after a current frame at time of a valid capture and record request, desired spatial characteristics of captured frames, or combinations thereof. Such spatial characteristics of the video frames can include, but are not limited to, interlaced or de-interlaced, native resolution or scaled, raw or noise filtered, natural or color corrected, 2D or 3D, or a combination thereof.

In certain examples, the system can include one or more profiles of the above parameters for preprogramming and selection by a user (e.g., user preferences as discussed above). For example, a user can specify a set of preferred values for the parameters for a certain procedure and have the variables preprogrammed in a profile of the system. Upon starting the procedure, the user can select the profile. The system can automatically populate the parameters with the preferred values.

In certain examples, profiles or combinations of programmable parameters can be grouped into functional "profiles" including content-based profiles and user-based profiles. Content-based profiles can associate ideal behavior with real-time assessment of live video content, such as computed frame-to-frame difference, computed motion estimation, or bad frame skip and detect. In some examples, the association of the ideal behavior with the real-time assessment of the live video content can be made using a trained machine learning algorithm. Computed frame-to-frame difference assessment can adjust temporal spacing such as increasing periods of temporal spacing for low frame-to-frame difference and decreasing periods of temporal spacing for high frame-to-frame difference. Computer frame-to-frame difference assessment can adjust total frames captured such as by decreasing total fames captured for periods of low frame-to-frame difference and increasing total frames captured for periods of high frame-to-frame difference.

Computed motion estimation can adjust the number of past frames captured by increasing the number of past frames captured for periods of high frame-to-frame motion difference. Bad frame detect and skip can assess the programmatically captured frames and can select a neighboring frame if a programmatically captured frame has issues. For example, if frame spacing exceeds a designated limit (two, for example), a frame assessed by an algorithm to be overexposed might be skipped in favor of a better one to either side. As another example, a different frame may be selected when a programmatically captured frame has exceedingly low image contrast, such as frames compromised by common endoscopic occurrences including smoke, bubbles, near-lens obstruction, or instantaneous motion.

User-based profiles of parameters can associate desired behavior with user-driven policies or assumptions including for clinical specialty or modality, facility, or user. Clinical specialty or modality profiles can be set up when a profile is identified that works well for, for example, a voice clinic, a colonoscopy, or for procedures using particular instruments such as camera-based microsurgery instruments. Facility driven profiles can allow for a default setup for identified circumstances. For example, a facility driven profile may have default parameter settings for all of the facility's operating rooms. User-driven profiles can allow for profiles having predetermined parameter values associated with certain personnel. For example, a practitioner can create a profile that includes video capture preferences. During procedures, the practitioner can specify the profile, which in turn can instruct the system to automatically set the video capture parameters to the preferences saved in the profile.

In certain examples, the trained machine-learning algorithm can adjust, alter, update, or the like, the programmable parameters, the content-based profiles, or the user-based profiles based on the assessment of the live video. For example, if a particular video frame would be captured in response to a triggering event/capture request based on a doctor's preference, but the system determines that particular frame is bad (e.g., overexposed, compromised, or the like), the system can skip that frame and capture a neighboring frame.

Figure 4:
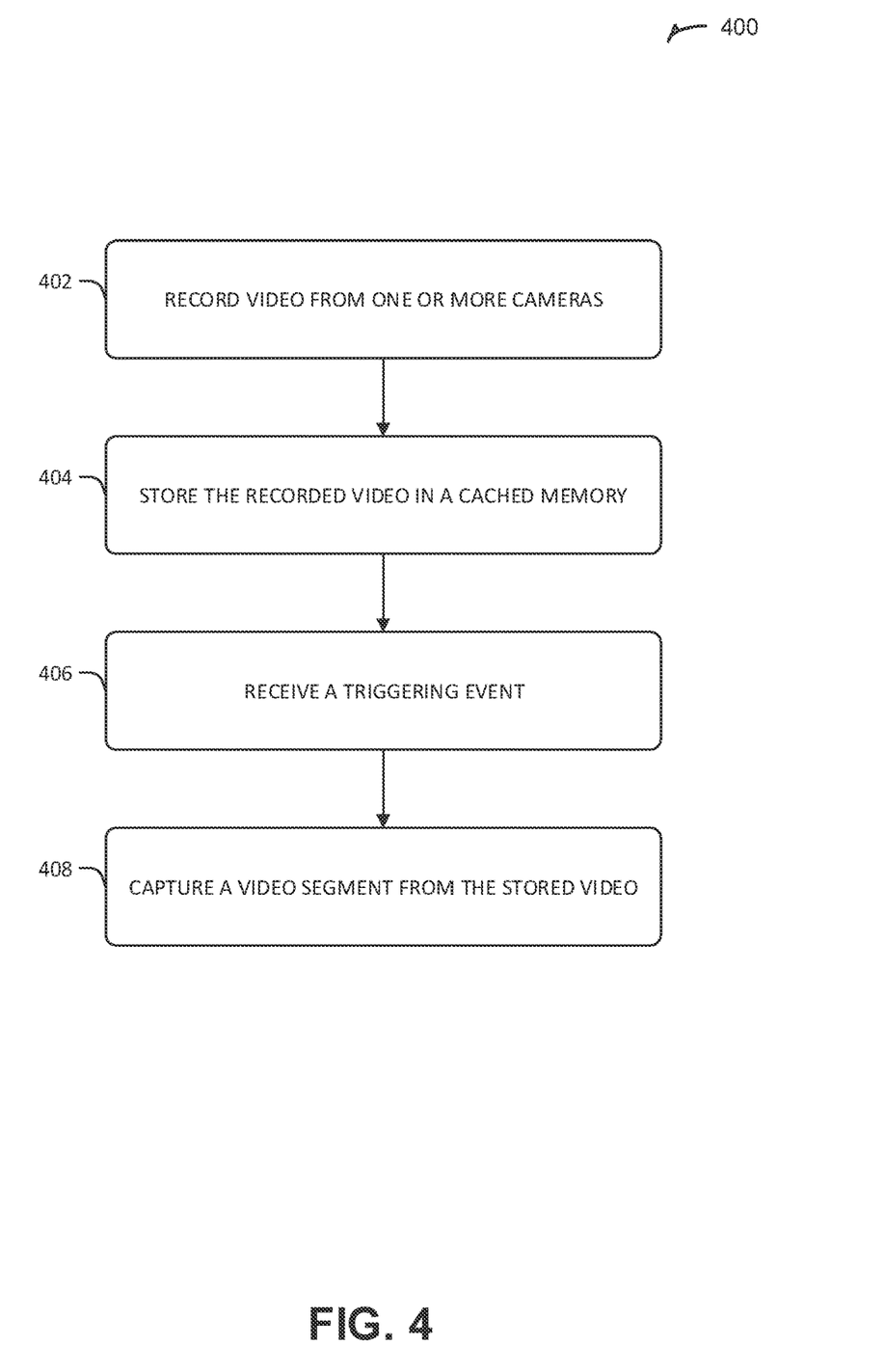
FIG. 4 illustrates a flowchart of an example method for image capture during a medical procedure.

FIG. 4 illustrates a flowchart of an example method 400 for image capture during a medical procedure. Operation 402 can include recording video from one or more video sources. The video sources can be those such as cameras 106 (e.g., cameras located in the integrated operating room 100 such as above the operating bed 102) or cameras that are attached to one or more of the procedure devices/instruments such as an endoscope, laparoscope, or the like. Operation 404 can include storing the recorded video in a cached memory as stored video. For example, when a medical procedure begins, a video from one or more of the video sources can start recording and be stored in cached memory of the system controller 116, the video manager 202, on a server connected to the closed network 218, or the like. The cached memory can temporarily store video recorded by one or more of the video sources for a period of time, until the cache memory is full (at which point the video stored in cache memory can be overwritten with newly recorded video), or until the procedure ends.

Operation 406 can include receiving a triggering event. The triggering event can be an event (e.g., receiving a signal) that causes the system to capture video from the stored video. In an example, the triggering event can cause the system to start recording video from one or more video sources. For example, instead of the system recording and storing video when the medical procedure begins, the triggering event can initiate the recording of video from the video sources. The triggering event can be activated by the user, such as by operation of an actuator (e.g., a button, a foot pedal, or a switch) or through voice activation such as by a spoken command that can be picked up by a microphone located in the integrated operating room 100. In other examples, a controller such as the system controller 116 can automatically determine a triggering event. The automatically determined triggering event can be a camera attached to a procedure tool lingering on a target or a portion of anatomy during a medical procedure for an extended period of time. For example, the system can trigger the video capture system upon a determination that a camera attached to an endoscope is no longer moving. A determination that the camera is no longer moving can indicate that the physician is looking at a portion of anatomy, a target, or something of interest during the procedure.

Operation 408 can include, in response to the triggering event, capturing a video segment from the stored video. For example, in response to an actuation by a physician (or a determination by the system of something of interest during the procedure) the integrated system 200 can capture a video segment from the stored video. Prior to receiving the triggering event, one or more segments of the stored video can be buffered (e.g., video frames or segments having a time code before the triggering event). The buffered video frames/segments can be used to prepend the captured video segment started when the triggering event is received. When an event of interest is short or fleeting, it may be over by the time the trigger is received by the system. Thus, prepending the captured video segment with the buffered video segment can ensure that the event of interest is captured even if it is over by the time the trigger is received.

In some examples, the one or more buffered video segments can include a fixed length of the stored video (e.g., ten seconds, thirty seconds, or any other appropriate or desired length). In other examples, the buffered video segments can include a user modifiable length of the stored video. For example, the physician may specify a certain number of video frames to be buffered or a certain length of video to be buffered. In the case in which the buffered video segments include a user modifiable length, this modifiable length may be stored as a preference or in a profile for the user as discussed above. In an example in which the triggering event causes video from one or more video sources to start recording, the video can be prepended with the buffered video that occurs before the triggering event is received. In such a situation, video from the video sources can be buffered, but not stored as stored video. Then, in response to the triggering event and the initiation of a video recording, at least a portion of the buffered video can be prepended to the initiated video recording to create a starting point of the triggered video.

Figure 5:
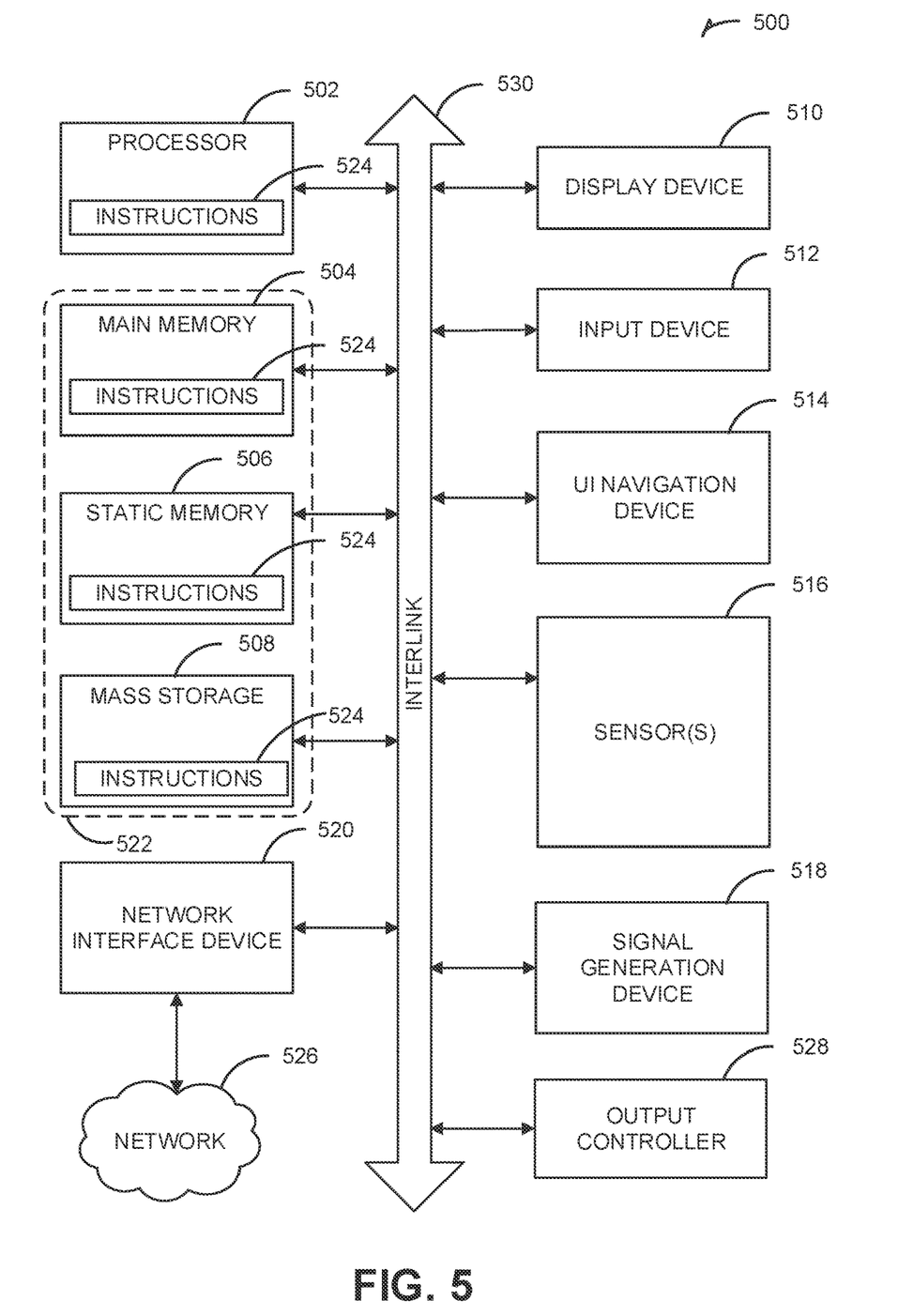
FIG. 5 is a block diagram illustrating an example of a machine upon which one or more embodiments may be implemented.

FIG. 5 illustrates a block diagram of an example machine 500 upon which any one or more of the techniques (e.g., methodologies) discussed herein may perform. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 502 (e.g., a central processing unit (CPU), a graphics processing unit (GPU), a hardware processor core, field programmable gate array (FPGA), or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a non-transitory machine-readable medium 522 on which is stored one or more sets of data structures or instructions 524 (e.g., software) embodying or used by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding, or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 500, and includes digital or analog communications signals or other intangible medium to facilitate communication of such software.

Figure 6:
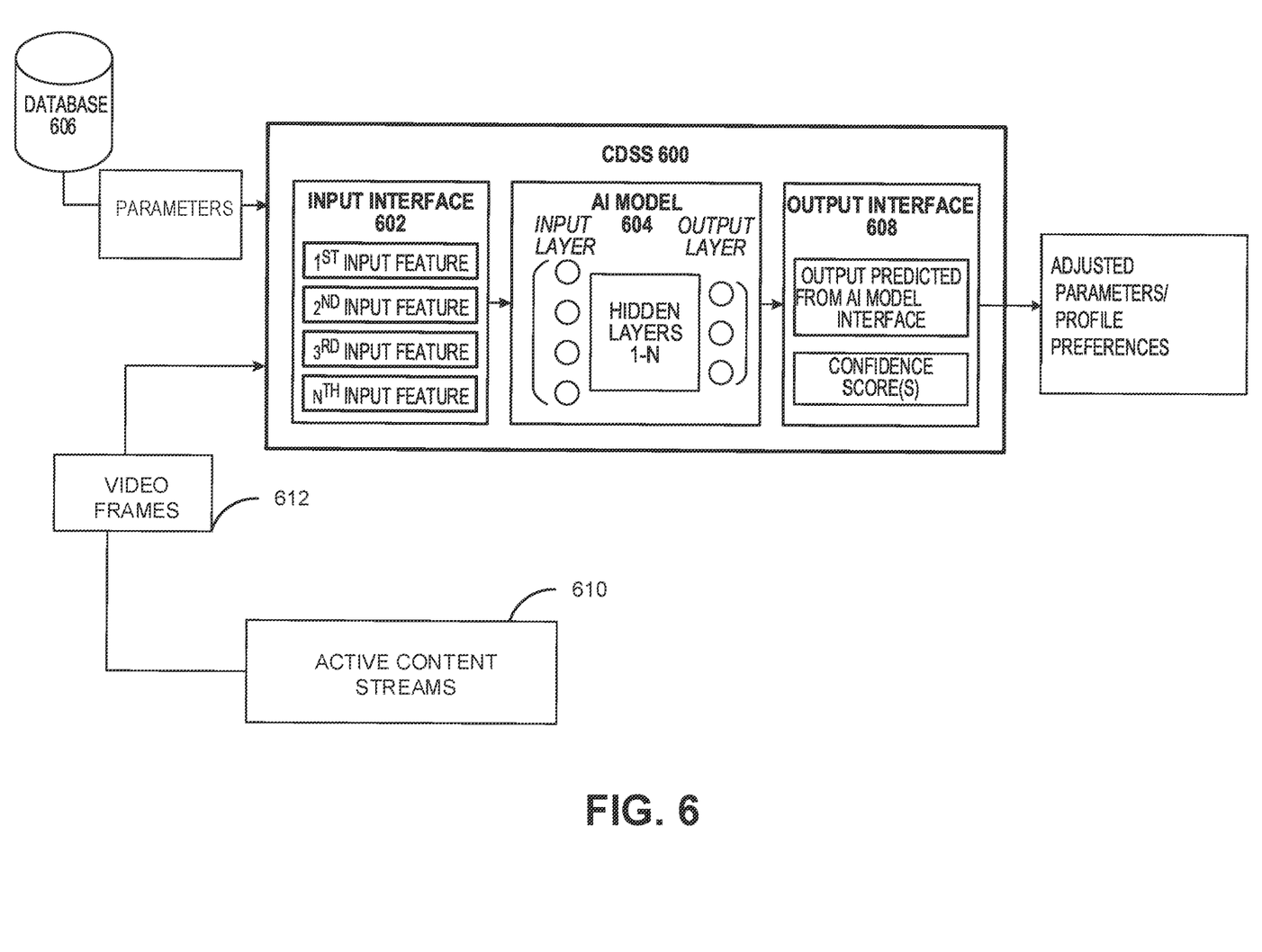
FIG. 6 illustrates a schematic diagram of an exemplary computer-based clinical decision support system (CDSS).

FIG. 6 illustrates a schematic diagram of an exemplary computer-based clinical decision support system (CDSS) 600 that is configured to adjust a preprogrammed parameter or profile setting based on a real-time assessment of a live video stream from one or more video sources. In various embodiments, the CDSS 600 includes an input interface 602 through which preprogrammed parameters for video capture which are specific to a patient are provided as input features to an artificial intelligence (AI) model 604, a processor, such as processor 502 which performs an inference operation in which the preprogrammed parameters and the live video are applied to the AI model to generate adjusted parameter or adjusted profile setting, and an output interface 608 through which the adjusted parameter or adjusted profile preference/setting is communicated to a user, e.g., a clinician.

In some embodiments, the input interface 602 may be a direct data link between the CDSS 600 and one or more medical devices that generate at least some of the input features. For example, the input interface 602 may transmit preprogrammed parameters or the profile settings directly to the CDSS 600 during a therapeutic and/or diagnostic medical procedure. In an example, the preprogrammed parameters or profile settings can be stored in a database 606. Additionally, or alternatively, the input interface 602 may be a classical user interface that facilitates interaction between a user and the CDSS 600. For example, the input interface 604 may facilitate a user interface through which the user may manually enter the preprogrammed parameter or the profile setting. Additionally, or alternatively, the input interface 602 may provide the CDSS 600 with access to an electronic patient record or the user/facility profiles/preferences discussed above from which one or more input features may be extracted. In any of these cases, the input interface 602 is configured to collect one or more of the following input features in association with one or more of a specific patient, a specific physician, a specific procedure, a specific room, or a specific facility, on or before a time at which the CDSS 600 is used to assess the preprogrammed parameters and/or profile settings and adjust the parameters/profile settings based on a real-time assessment of the live video streams from one or more video sources.

An example of an input feature can include a number of active content streams 610 from which images are to be captured. As discussed above, the integrated operating room 100 can contain multiple video sources. Video streams from one or more video sources, such as cameras 106 located within the integrated operating room 100 or one or more video sources attached to, coupled to, or the like, one or more medical instruments used during a medical procedure, can be captured during a procedure. Video frames 612 from the active content streams 610 can then be input into the input interface 602 and processed by the CDSS 600.

An example of an input feature can include how many images, and from which specific video sources the images may be captured during a procedure. These selections may be specific to the procedure, specific to the room the procedure is being performed in, a specific preference of the physician performing the procedure, or the like.

An example of an input feature can include a desired temporal spacing between the captured frames of video (e.g., whether the system should "skip" one or more frames.

An example of an input feature can include a desired temporal distribution of captured images.

An example of an input feature can include a number of captured frames before and after the nominal/"current" frame at the time of a valid capture and record request or triggering event.

An example of an input feature can include interlacing or de-interlacing of video frames.

An example of an input feature can include native video resolution or scaled video resolution.

An example of an input feature can include a raw image or a filtered image.

An example of an input feature can include natural image color or color corrected images.

An example of an input feature can include Image dimension (e.g., two-dimensional image or three-dimensional image).

An example of an input feature can include intended luminance transfer function (e.g., standard dynamic range or high dynamic range).

Based on one or more of the above input features, the processor 502 performs an inference operation using the AI model 604 to generate the adjusted parameters. For example, input interface 602 may deliver the one or more of the input features listed above into an input layer of the AI model 604 which propagates these input features through the AI model 604 to an output layer. The AI model 604 can provide a computer system the ability to perform tasks, without explicitly being programmed, by making inferences based on patterns found in the analysis of data. The AI model 604 explores the study and construction of algorithms (e.g., machine-learning algorithms) that may learn from existing data and make predictions about new data. Such algorithms operate by building an AI model from example training data in order to make data-driven predictions or decisions expressed as outputs or assessments.

There are two common modes for machine learning (ML): supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled and allowing the algorithm to act on that information without guidance. Unsupervised ML is useful in exploratory analysis because it can automatically identify structure in data.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model 604 may be trained continuously or periodically prior to performance of the inference operation by the processor 502. Then, during the inference operation, the patient specific input features provided to the AI model 604 may be propagated from an input layer, through one or more hidden layers, and ultimately to an output layer that corresponds to the adjusted parameters or profile preferences. For example, when evaluating the live video feeds, the system can determine that the temporal spacing of frames captured or the total amount of frames captured should be adjusted based on a factor such as frame-to-frame difference of the video frames. Similarly, the system can adjust what frames are captured or skipped if a programmatically captured frame is damaged, unclear, obstructed, overexposed, has a low image contrast, is otherwise unusable, or the like.

During and/or subsequent to the inference operation, the adjusted parameters/preferences may be communicated to the user via the output interface 608 (e.g., a user interface (UI)). In another example, the adjusted parameters/preferences can automatically cause an apparatus connected to the processor 502 to perform a desired action. For example, the CDSS 600 can output a report of any of the parameters or preferences that are adjusted during the medical procedure and why the adjustments were made (e.g., because of bad frames, frame-to-frame difference, or the like). Additionally or alternatively, the CDSS 600 can cause video being captured from a camera connected to one of the medical instruments (e.g., an endoscope) to be turned on or off based on the live video feed. For example, if the camera is lingering, pausing, or the like on a certain feature, portion of anatomy, object, piece of tissue or the like, the CDSS 600 can cause the video of the camera on the scope to be captured until the scope is determined to be moving again. In some examples, the CDSS 600 can alter the video processing applied to a source (e.g., adjusting the brightness level of an image or filtering an image).

The aspects of the system described above can assist the ongoing practice of medical care by allowing doctors or other personnel within an operating room to capture interesting moments of a procedure that can be easily accessed after-the-fact for a variety of purposes. Those purposes can include, but are not limited to, reflecting on and studying the care of a patient to better serve the patient, train others on procedures and best practices, train others on protocols whiting the operating room especially when unexpected events occur, or combination thereof. It is understood that the above described techniques focused on capturing video feeds, however, in certain examples, when a user initiates a capture and record event, audio or textual information, such as from instruments, can also be captured and recorded alone or in addition to one or more video feeds.

ADDITIONAL NOTES AND EXAMPLES

Example 1 is a system for image capture during a medical procedure, the system comprising: at least one processor; and memory coupled to the at least one processor, the memory configured to store instructions that, when executed by the at least one processor, cause the at least one processor to execute operations, the operations comprising: recording video from one or more video sources; storing the recorded video in a cached memory as stored video; receiving a triggering event; and in response to the triggering event, capturing a video segment from the stored video.

In Example 2, the subject matter of Example 1 optionally includes wherein the operations further comprise: prior to receiving the trigger event, buffering one or more segments of the stored video; and storing a modified video that includes the captured video segment prepended with the one or more buffered segments.

In Example 3, the subject matter of Example 2 optionally includes wherein the operations further comprise: continuously recording a cached video stream from the one or more video sources; and prepending one or more video frames of the cached video stream having a time code occurring prior to the triggering event.

In Example 4, the subject matter of any one or more of Examples 2-3 optionally include wherein the operations further comprise: 'storing a video capture window of time of the recorded video, the video capture window of time including at least a portion of the one or more buffered segments.

In Example 5, the subject matter of any one or more of Examples 2-4 optionally include wherein the one or more buffered segments includes a fixed length of the stored video.

In Example 6, the subject matter of any one or more of Examples 2-5 optionally include wherein the one or more buffered segments includes a user-modifiable length of the stored video.

In Example 7, the subject matter of any one or more of Examples 2-6 optionally include wherein the one or more buffered segments has a length that depends on a recognized event of the medical procedure.

In Example 8, the subject matter of any one or more of Examples 1-7 optionally include wherein the triggering event is activated by a user.

In Example 9, the subject matter of Example 8 optionally includes wherein the triggering event includes at least one of: operation of an actuator, or a voice activation.

In Example 10, the subject matter of any one or more of Examples 1-9 optionally include wherein the operations further comprise: capturing a plurality of frames of the stored video, the plurality of frames extending over a time window that includes the triggering event; and storing one or more still images from the plurality of frames of the stored video.

In Example 11, the subject matter of Example 10 optionally includes wherein capturing the plurality of frames includes selecting the time window based on at least one of:

a value controlling the number of active content streams from which images are to be captured, a desired temporal distribution of captured images, a temporal spacing between captured frames of video, a number of captured frames before and after a current frame at time of a valid capture and record request, desired spatial characteristics of captured frames, or combinations thereof.

Example 12 is a system for image capture during a medical procedure, the system comprising: at least one processor; and memory coupled to the at least one processor, the memory configured to store instructions that, when executed by the processor, cause the at least one processor to execute operations, the operations comprising: recording video from one or more video sources; storing the recorded video in a cached memory as stored video; receiving one or more predetermined parameters for capturing a video segment; receiving a triggering event; in response to the triggering event, capturing the video segment; prior to receiving the triggering event, buffering one or more segments of the stored video based on the one or more predetermined parameters; and storing a modified video that includes the captured video segment prepended with the one or more buffered video segments based on the one or more predetermined parameters; capturing a plurality of frames of the stored video based on the one or more predetermined parameters, the plurality of frames extending over a time window that includes the triggering event; storing one or more still images from the plurality of frames of the stored video.

In Example 13, the subject matter of Example 12 optionally includes wherein the operations further comprise: adjusting, based on real-time assessment of the recorded video from the one or more video sources, at least one of the one or more buffered segments or the captured plurality of frames of the stored video.

In Example 14, the subject matter of Example 13 optionally includes wherein the adjustment is made by a trained learning model and based on one or more of: low frame-to-frame difference, high frame-to-frame difference, an amount of motion, an amount of frame exposure, an amount of image contrast, a type of clinical procedure, or a combination thereof.

In Example 15, the subject matter of any one or more of Examples 12-14 optionally include wherein the operations further comprise: capturing a plurality of frames of the stored video, the plurality of frames extending over a time window that includes the triggering event, wherein capturing the plurality of frames includes selecting the time window based at least one of: a value controlling the number of active content streams from which images are to be captured, a desired temporal distribution of captured images, a temporal spacing between captured frames of video, a number of captured frames before and after a current frame at time of a valid capture and record request, a desired spatial characteristics of captured frames, or combinations thereof; and storing one or more still images from the plurality of frames of the stored video.

Example 16 is a method for image capture during a medical procedure, the method comprising: recording video from one or more video sources; storing the recorded video in a cached memory as stored video; receiving a triggering event; and in response to the triggering event, capturing a video segment from the stored video.

In Example 17, the subject matter of Example 16 optionally includes prior to receiving the triggering event, buffering one or more segments of the stored video; and storing a modified video that includes the captured video segment prepended with the one or more buffered segments.

In Example 18, the subject matter of Example 17 optionally includes continuously recording a cached video stream from the one or more video sources; and prepending one or more video frames of the cached video stream having a time code occurring prior to triggering event.

In Example 19, the subject matter of any one or more of Examples 16-18 optionally include capturing a plurality of frames of the stored video, the plurality of frames extending over a time window that includes the triggering event; and storing one or more still images from the plurality of frames of the stored video.

In Example 20, the subject matter of Example 19 optionally includes wherein capturing the plurality of frames includes selecting the time window based on at least one of: a value controlling the number of active content streams from which images are to be captured, a desired temporal distribution of captured images, a temporal spacing between captured frames of video, a number of captured frames before and after a current frame at time of a valid capture and record request, a desired spatial characteristics of captured frames, or combinations thereof.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for image capture during an internal medical procedure performed within a body of a patient, the system comprising:
   at least one processor; and
   memory coupled to the at least one processor, the memory configured to store instructions that, when executed by the at least one processor, cause the at least one processor to execute operations, the operations comprising:
      recording video from one or more video sources, the recording occurring during the internal medical procedure performed within the body of the patient;
      storing the recorded video in a cached memory as stored video;
      performing an analysis of the stored video to detect a specific event, occurring during the internal medical procedure performed within the body of the patient, as a triggering event; and
      in response to detecting the triggering event, capturing a video segment from the stored video based on an onset and cessation of the triggering event.

2. The system of claim 1, wherein the operations further comprise:
   prior to receiving the triggering event, buffering one or more segments of the stored video; and
   storing a modified video that includes the captured video segment prepended with the one or more buffered segments.

3. The system of claim 2, wherein the operations further comprise:
   continuously recording a cached video stream from the one or more video sources; and
   prepending one or more video frames of the cached video stream having a time code occurring prior to the triggering event.

4. The system of claim 2, wherein the operations further comprise:
   storing a video capture window of time of the recorded video, the video capture window of time including at least a portion of the one or more buffered segments.

5. The system of claim 2, wherein the one or more buffered segments includes a fixed length of the stored video.

6. The system of claim 2, wherein the one or more buffered segments includes a user-modifiable length of the stored video.

7. The system of claim 2, wherein the one or more buffered segments has a length that depends on a recognized event of the medical procedure.

8. The system of claim 1, wherein the specific event is determined based at least in part on information stored in one or more profiles, wherein the analysis of the stored video is performed in real-time to compare the stored video with the information in the one or more profiles, and wherein the triggering event includes an activation by a user, and wherein the internal medical procedure is an endoscopic medical procedure.

9. The system of claim 8, wherein the triggering event includes at least one of: operation of an actuator, or a voice activation.

10. The system of claim 1, wherein the operations further comprise:
    capturing a plurality of frames of the stored video, the plurality of frames extending over a time window that includes the triggering event, with one or more frames of the plurality of frames occurring before the triggering event and one or more frames of the plurality of frames occurring after the triggering event; and
    storing one or more still images from the plurality of frames of the stored video.

11. The system of claim 10, wherein capturing the plurality of frames includes selecting the time window based on at least one of: a value controlling a number of active content streams from which images are to be captured, a desired temporal distribution of captured images, a temporal spacing between captured frames of video, a number of captured frames before and after a current frame at time of a valid capture and record request, desired spatial characteristics of captured frames, or combinations thereof.

12. The system of claim 1, wherein the at least one processor is configured to detect the specific medical event based on one or more visual cues in the recorded video, and wherein the one or more visual cues include at least one of smoke, bubbles, a near-lens obstruction, or motion in a field of view of an imaging sensor.

13. A system for image capture during an internal medical procedure performed within a body of a patient, the system comprising:
    at least one processor; and
    memory coupled to the at least one processor, the memory configured to store instructions that, when executed by the at least one processor, cause the at least one processor to execute operations, the operations comprising:
       capturing, during the internal medical procedure, video of the internal medical procedure from one or more video sources;
       displaying a video stream of the internal medical procedure captured by the one or more video sources in substantially real-time;
       storing, concurrently with the displaying, the captured video of the internal medical procedure in a cached memory as stored video;
       performing an analysis of the stored video to detect a specific event occurring during the internal medical procedure as a triggering event;
       receiving one or more predetermined parameters for capturing a video segment;
       in response to detecting the triggering event, capturing the video segment;
       prior to receiving the triggering event, buffering one or more segments of the stored video based on the one or more predetermined parameters;
       storing a modified video that includes the captured video segment prepended with the one or more buffered video segments based on the one or more predetermined parameters;

capturing a plurality of frames of the stored video based on the one or more predetermined parameters and based on an onset and cessation of the triggering event, the plurality of frames extending over a time window that includes the triggering event, with one or more frames of the plurality of frames occurring before the triggering event and one or more frames of the plurality of frames occurring after the triggering event; and storing one or more still images from the plurality of frames of the stored video.

14. The system of claim 13, wherein the operations further comprise:

adjusting, based on real-time assessment of the captured video of the internal medical procedure from the one or more video sources, at least one of the one or more buffered segments or the captured plurality of frames of the stored video.

15. The system of claim 14, wherein the adjustment is made by a trained learning model and based on one or more of: low frame-to-frame difference, high frame-to-frame difference, an amount of motion, an amount of frame exposure, an amount of image contrast, a type of clinical procedure, or a combination thereof.

16. The system of claim 13, wherein the operations further comprise:

capturing a plurality of frames of the stored video, the plurality of frames extending over a time window that includes the triggering event, wherein capturing the plurality of frames includes selecting the time window based at least one of: a value controlling a number of active content streams from which images are to be captured, a desired temporal distribution of captured images, a temporal spacing between captured frames of video, a number of captured frames before and after a current frame at time of a valid capture and record request, a desired spatial characteristics of captured frames, or combinations thereof; and storing one or more still images from the plurality of frames of the stored video.

17. A method for image capture during an internal medical procedure performed within a body of a patient, the method comprising:

recording video from one or more video sources, the recording occurring during the internal medical procedure performed within the body of the patient;

storing the recorded video in a cached memory as stored video;

performing an analysis of the stored video to detect a specific event occurring during the internal medical procedure performed within the body of the patient as a triggering event; and in response to detecting the triggering event, capturing a video segment from the stored video based on an onset and cessation of the triggering event.

18. The method of claim 17, further comprising:

prior to receiving the triggering event, buffering one or more segments of the stored video; and storing a modified video that includes the captured video segment prepended with the one or more buffered segments.

19. The method of claim 18, further comprising:

continuously recording a cached video stream from the one or more video sources; and prepending one or more video frames of the cached video stream having a time code occurring prior to triggering event.

20. The method of claim 17, further comprising:

capturing a plurality of frames of the stored video, the plurality of frames extending over a time window that includes the triggering event; and storing one or more still images from the plurality of frames of the stored video.

21. The method of claim 20, wherein capturing the plurality of frames includes selecting the time window based on at least one of: a value controlling a number of active content streams from which images are to be captured, a desired temporal distribution of captured images, a temporal spacing between captured frames of video, a number of captured frames before and after a current frame at time of a valid capture and record request, a desired spatial characteristics of captured frames, or combinations thereof.

* * * * *

UNITED STATES PATENT AND TRADEMARK OFFICE
CERTIFICATE OF CORRECTION

PATENT NO. : 12,343,219 B2  
APPLICATION NO. : 17/585176  
DATED : July 1, 2025  
INVENTOR(S) : Landfors et al.

Page 1 of 1

It is certified that error appears in the above-identified patent and that said Letters Patent is hereby corrected as shown below:

In the Claims

In Column 18, Line 33, in Claim 12, after "specific", delete "medical"

Signed and Sealed this
Twenty-sixth Day of August, 2025

Coke Morgan Stewart
*Acting Director of the United States Patent and Trademark Office*